United States Patent [19]

Molloy et al.

[11] Patent Number: 4,584,404
[45] Date of Patent: * Apr. 22, 1986

[54] SUBSTITUTED PHENOXYPHENYLPROPLY DIMETHYLAMINES

[75] Inventors: Bryan B. Molloy, North Salem; Klaus K. Schmiegel, Indianapolis, both of Ind.

[73] Assignee: Eli Lilly and Company, Indianapolis, Ind.

[*] Notice: The portion of the term of this patent subsequent to Feb. 2, 1999 has been disclaimed.

[21] Appl. No.: 544,654

[22] Filed: Oct. 24, 1983

Related U.S. Application Data

[60] Continuation-in-part of Ser. No. 872,147, Jan. 25, 1978, abandoned, which is a division of Ser. No. 432,379, Jan. 10, 1974, Pat. No. 4,314,081.

[51] Int. Cl.$^4$ .................. A61K 31/205; C07C 93/06
[52] U.S. Cl. ........................... 564/347; 260/501.18; 514/554; 514/566; 514/651; 564/342; 564/366
[58] Field of Search ............... 564/347; 260/501.18; 424/332, 316

[56] References Cited

U.S. PATENT DOCUMENTS

| | | | |
|---|---|---|---|
| 2,683,742 | 7/1954 | Cusic | 260/567.6 |
| 3,106,564 | 10/1963 | Fleming et al. | 260/326.5 |
| 3,132,179 | 5/1964 | Clarke | 260/570.6 |
| 3,253,040 | 5/1968 | Potter et al. | 260/584 |
| 4,018,895 | 4/1977 | Molloy et al. | 424/330 |
| 4,194,009 | 3/1980 | Molloy et al. | 424/330 |
| 4,314,081 | 2/1982 | Molloy et al. | 564/347 |

OTHER PUBLICATIONS

Yoshida et al., Yakugaku Zasshi, 93, 508–518 (1973) "Yoshida I".
Yoshida et al., IBID, 519–528 "Yoshida II".

*Primary Examiner*—Robert V. Hines
*Attorney, Agent, or Firm*—James L. Rowe; Arthur R. Whale

[57] ABSTRACT

Selective biogenic amine uptake inhibitors, 3-substituted phenyloxy-3-phenylpropyldimethylamines.

5 Claims, No Drawings

SUBSTITUTED PHENOXYPHENYLPROPLY DIMETHYLAMINES

CROSS-REFERENCE

This application is a continuation-in-part of our co-pending application Ser. No. 872,147 filed Jan. 25, 1978 and now abandoned which was a division of our then co-pending application Ser. No. 432,379 filed Jan. 10, 1974, now U.S. Pat. No. 4,314,081, issued Feb. 2, 1982.

BACKGROUND OF THE INVENTION

Tertiary 2-phenoxy-2-phenylethylamines constitute the subject matter of U.S. Pat. No. 3,106,564. The compounds are said to be useful pharmacological agents exhibiting activity on the central nervous system including useful application as analeptic agents without significant effect on respiration. The compounds are also said to have a high order of activity as antihistaminic and anticholinergic agents. Several tertiary 3-phenoxy-3-phenylpropylamines and quaternary ammonium compounds useful as mydriatic agents are disclosed in *J. Pharmaceutical Society,* Japan, 93, 508–519, 1144–53, 1154–61 (1973).

The use of 3-substituted phenoxy-3-phenyl dimethylamines in treating depression is claimed in applicants' U.S. Pat. No. 4,018,895 issued Apr. 19, 1977 and pharmaceutical formulations containing 3-substituted phenoxy-3-phenyl dimethylamines as the active ingredient are claimed in applicants' U.S. Pat. No. 4,194,009 issued Mar. 18, 1980. Both of these applications were divisions of Ser. No. 432,379, the grandparent of this application, now U.S. Pat. No. 4,314,081.

Ser. No. 432,379 disclosed compounds of the following structure

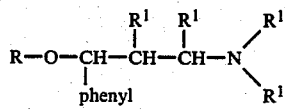

wherein each $R^1$ is independently H or methyl and R is naphthyl or

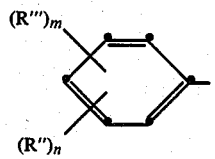

wherein R″ and R‴ are halo, $CF_3$, $C_{1-4}$ alkyl, $C_{1-3}$ alkoxy or $C_{3-4}$ alkenyl and n and m or 0, 1 or 2. The use and formulation claims of U.S. Pat. Nos. 4,018,895 and 4,194,009 specify an active drug of the identical structure, but the claims of U.S. Pat. No. 4,314,081 cover secondary amines of the formula

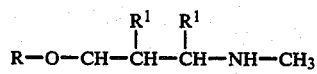

wherein $R^1$ has its previous scope but R is m or p-chlorophenyl, O, m or p-anisyl, phenyl, o or m-fluorophenyl, o or p-tolyl, 2,4-difluorophenyl or p-trifluoromethylphenyl. These claimed secondary amines each had unusually high activity in inhibiting uptake of serotonin (5HT) and norephinephine (NE) with less effect on dopamine uptake. Three compounds coming within the scope of claim 1 of the patent have been placed on clinical trial in humans as antidepressants. Two of these have been primarily NE uptake inhibitors, (a majority of the marketed antidepressant drugs increase NE concentrations in brain tissue by uptake inhibition or other mechanisms). The third drug, fluoxetine, —3-phenyl-3-(p-trifluoromethyl)phenoxypropyl methylamine—is a selective 5HT uptake inhibitor; ie., the ratio of the 50% inhibitory concentrations for 5HT uptake vs NE uptake was 0.06 to 20 or about 333 to 1. (See the top compound in Table 2 in any of the above referenced patents). No drug had previously been found with such selectivity for blocking 5HT uptake. Fluoxetine has proved to be a highly potent antidepressant in humans.

Among the dimethylamines covered by formula I above are several with a similar very high 5HT/NE uptake inhibition ratio or with a very low ratio. It is the purpose of this application to specify and claim these drugs.

SUMMARY OF THE INVENTION

In fulfillment of the above and other objects, this invention provides 3-phenoxy-3-phenylpropyl dimethylamines of the formula:

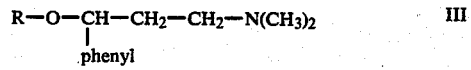

wherein R is p-chlorophenyl, p-methylphenyl(p-tolyl) or p-trifluoromethylphenyl; and acid addition salts thereof formed with pharmaceutically-acceptable acids.

In addition to the above three compounds described by formula III, which compounds are selective 5HT uptake inhibitors, there are related compounds which are selective NE uptake inhibitors, ie., prevent preferentially the uptake of NE. Predominant among these compounds is 3-o-tolyloxy-3-phenylpropyl dimethylamine (IV).

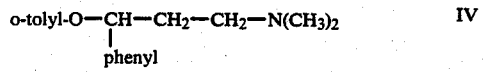

and its acid addition salts formed with non-toxic acids.

The pharmaceutically-acceptable salts of the amine bases represented by formulas III and IV include salts derived from inorganic acids such as: hydrochloric acid, nitric acid, phosphoric acid, sulfuric acid, hydrobromic acid, phosphorous acid and the like, as well as salts of non-toxic organic acids including aliphatic mono and dicarboxylic acids, phenyl-substituted alkanoic acids, hydroxy alkanoic and alkanedioic acids, aromatic acids, aliphatic and aromatic sulfonic acids, etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate, mandelate and the like salts.

The compounds of formulas III and IV in the form of their free bases are high boiling oils, but are white crystalline solids in the form of their acid addition salts. The compounds can be prepared in several ways. A particularly useful procedure for preparing compounds represented by the above formulas involves as a first step the reduction of β-dimethylaminopropiophenone (produced by a Mannich reaction) to N,N-dimethyl 3-phenyl-3-hydroxypropylamine. Replacement of the hydroxyl group with a halogen, such as chlorine, yields the corresponding N,N-dimethyl 3-phenyl-3-chloropropylamine. Reaction of this chloro compound with a suitably substituted phenol, as for example p-trifluoromethylphenol, produces a compound according to formula III or IV depending on the phenol employed.

This invention is further illustrated by the following specific examples:

EXAMPLE 1

Preparation of N,N-dimethyl-3-(p-trifluoromethylphenoxy)-3-phenylpropylamine About 600 g. of β-dimethylaminopropiophenone hydrochloride were converted to the corresponding free base by the action of 1.5N aqueous sodium hydroxide. The liberated free base was taken up in ether, the ether layer separated and dried, and the ether removed therefrom in vacuo. The residual oil comprising β-dimethylaminopropiophenone was dissolved in two liters of tetrahydrofuran, and the resulting solution added in dropwise fashion with stirring to a solution of four moles of diborane in four liters of tetrahydrofuran. The reaction mixture was stirred overnight at room temperature. An additional mole of diborane in one liter of tetrahydrofuran was added, and the reaction mixture stirred again overnight at room temperature. Next, two liters of aqueous hydrochloric acid were added to decompose any excess diborane present. The tetrahydrofuran was removed by evaporation. The resulting acidic solution was extracted twice with one liter portions of benzene, and the benzene extracts were discarded. The acidic solution was then made basic with an excess of 5N aqueous sodium hydroxide. The basic solution was extracted three times with two liter portions of benzene. The benzene extracts were separated and combined, and the combined extracts washed with saturated aqueous sodium chloride and then dried. Evaporation of the solvent in vacuo yielded 442 g. of N,N-dimethyl 3-phenyl-3-hydroxypropylamine.

A solution containing 442 g. of N,N-dimethyl 3-phenyl-3-hydroxypropylamine in 5 l. of chloroform was saturated with dry gaseous hydrogen chloride. 400 ml. of thionyl chloride were added to the chloroform solution at a rate sufficient to maintain reflux. Reflux was continued for an additional 5 hours. Evaporation of the chloroform and other volatile constituents from the reaction mixture in vacuo yielded N,N-dimethyl 3-phenyl-3-chloropropylamine hydrochloride which was collected by filtration. The filter cake was washed twice with 1500 ml. portions of acetone. The washed crystals weighed about 500 g., and melted at 181°–183° C. with decomposition. An additional 30 g. of compound were obtained from the acetone wash by standard crystallization procedures. The structure of the above compound was verified by NMR and titration.

A solution of 50 g. of p-trifluoromethylphenol, 12 g. of solid sodium hydroxide and 400 ml. of methanol was prepared in a one liter round-bottom flask equipped with magnetic stirrer, condenser and drying tube. Next, 29.8 g. of N,N-dimethyl 3-phenyl-3-chloropropylamine hydrochloride were added. The resulting reaction mixture was refluxed for about 5 days and then cooled. The methanol was removed by evaporation, and the resulting residue taken up in a mixture of ether and 5N aqueous sodium hydroxide. The ether layer was separated and washed twice with 5N aqueous sodium hydroxide and three times with water. The ether layer was dried, and the ether removed by evaporation in vacuo to yield as a residue N,N-dimethyl 3-(p-trifluoromethylphenoxy)-3-phenylpropylamine.

The free base was converted to the corresponding oxalate salt by dissolving 32 g. of the amine in ethyl acetate to which was added a solution of 9 g. of oxalic acid also in ethyl acetate. N,N-dimethyl-3-p-trifluoromethylphenoxy-3-phenylpropylamine oxalate thus formed melted at 117°–119° C. with decomposition after recrystallization from ethyl acetate.

Analysis: Calc.: C, 58.11; H, 3.36; N, 3.39; F, 13.79. Found: C, 58.19; H, 3.49; N, 3.59; F, 13.85.

The following N,N-dimethyl substituted phenoxy-3-phenylpropylamines were prepared by the above procedures.

N,N-dimethyl 3-(o-tolyloxy)-3-phenylpropylamine oxalate which melted at 160°–162° C. after recrystallization from a methanol-isopropanol solvent mixture.

Analysis: Calc.: C, 66.84; H, 7.01; N, 3.90. Found: C, 66.82; H, 7.07; N, 4.17.

N,N-dimethyl 3-phenyl-3-(p-chlorophenoxy)-propylamine oxalate: melting point=139°–141° C.

Analysis: Calc.: C, 60.08; H, 5.84; N, 3.69; Cl, 9.33. Found: C, 60.34; H, 5.95; N, 3.88; Cl, 9.61.

N,N-dimethyl 3-(p-tolyloxy)-3-phenylpropylamine oxalate: melting point=145°–147° C.

Analysis: Calc.: C, 66.84; H, 7.01; N, 3.90. Found: C, 66.61; H, 7.01; N, 4.06.

EXAMPLE 2

Preparation of Salts

Salts of the free bases of this invention, other than the oxalate salts whose preparation is illustrated in Example 1, are prepared by dissolving the free base in ether and adding an equivalent of a suitable acid, also in ether. The salts thus formed, as for example the maleate salts, are insoluble in ether and can be isolated by filtration. Alternatively, the amine base can be dissolved in ethanol and an equivalent of the acid added as an ethanolic solution. In this instance, since the salts thus formed are usually soluble in the reaction mixture, they are isolated by evaporation of the solvent in vacuo. Salts which can be formed by the above procedure include the sulfate, hydrobromide, hydrochloride, phosphate, hydrogen phosphate, dihydrogen phosphate, acetate, methanesulfonate, succinate, tartrate, citrate, benzoate, and p-toluene sulfonate salts.

As indications of their psychotropic activity, the compounds of this invention have been found to block the uptake of various physiologically active monoamines. This blockade is shown both in vitro with radioactive labelled compounds to determine the amount of monoamine uptake by synaptosomes from rat brain, and in vivo by a variety of methods. Among the physiologically active monoamines whose uptake is blocked by the compounds of this invention are included particularly serotonin (5HT) and norepinephrine(3,4-dihydroxyphenylethanolamine). While all of the compounds represented by Formula I above block the uptake of one or both monoamines, certain of them possess a unique selectivity in that they block the uptake of one of the monoamines to a far greater extent than they do the uptake of the other, or of dopamine. Tables 1 and 2 which follow set forth the results of some of the in vitro determinations of the blockade of monoamine uptake by the compounds of this invention. In the tables, column 1 gives the R substituent on the 3-phenylpropylamine and columns 2-4, the concentration in micrograms per ml. that blocks the uptake by 50 percent of the monoamines—norepinephrine, serotonin, and dopamine. At the head of each column is given the concentration of the particular monoamine used in the experiment.

TABLE 1

$$R-CH-CH_2-CH_2-N(CH_3)_2$$
$$|$$
$$C_6H_3$$

| R | Concentration in mcg./ml. that blocks 50% of amine uptake | | |
|---|---|---|---|
|   | Norepinephrine 0.48 µM | Serotonin 0.1 µM | Dopamine 0.2 µM |
| p-chlorophenoxy | .3 | .03 | 1.3 |
| p-trifluoromethylphenyloxy | 70 | .16 | >100 |
| o-tolyloxy | .35 | .2 | 0.8 |
| p-tolyloxy | .015 | .4 | >100 |

Compounds according to formulas III or IV which have 5HT/NE uptake ratios significantly different from 1 are presented in Table 2 below.

TABLE 2

NE/5HT IC$_{50}$ UPTAKE RATIOS

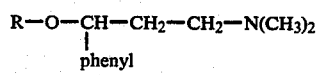

| Sub | Ratio NE/5HT |
|---|---|
| o-CH$_3$ | .5 |
| p-CH$_3$ | 5.83 |
| p-Cl | 9.88 |
| p-CF$_3$ | 7.19 |

In addition to their usefulness as psychotropic agents, the compounds of formula may also find use in treating disorders of sleep, sexual performance, appetite, muscular function, and pituitary function. All of these physiologic functions have been shown to be subject to influence by brain serotoninergic neural systems.

It is apparent from the above data that the compounds have NE/5HT IC$_{50}$ uptake inhibitor ratios that are greater or lower than 1, particularly the p-CF$_3$ compound where the ratio is 7.19. Preferential inhibitors of 5HT uptake obviously will have a different physiological effect compared to a drug with approximately equal uptake inhibition of 5HT and NE (ratio ~1) or one that preferentially blocks NE, since 5HT and NE have different functions and affect different sites in the brain. Many of the prior art antidepressants have 5HT/NE uptake inhibition ratios of about 1 and are useful in treating patients with depleted NE and 5HT levels. While such marketed drugs, and unmarketed drugs with similar NE/5HT uptake inhibition ratios, are clearly useful in treating depression, the more selective drugs of this invention, particularly those that block 5HT uptake preferentially, may be more useful in treating certain patients because of the different spectrum of side effects in that NE levels in the brain remain normal. On the other hand, in many depressed patients the brain serotonin levels may be more or less normal but NE is depleted. Here, the drug of formula IV, which drug blocks NE preferentially, may be specially useful.

In testing humans suffering from various psychoses having a depressive component, the compounds of formulas III and IV can be given orally at parenterally. In either instance, it is preferred to use a pharmaceutically-acceptable acid addition salt of the compound formed. For purposes of oral administration, the salt can be mixed with standard pharmaceutical excipients and placed in telescoping gelatin capsules. Alternatively, the compound can be mixed with starch, binders, etc. and formulated into tablets, which tablets may be scored for ease of divided dosage administration. For parenteral administration, a water soluble salt of a compound of this invention, which salt is also pharmaceutically-acceptable, is dissolved in an isotonic solution and administered intramuscularly, intravenously or subcutaneously. For chronic administration, the oral pharmaceutical forms are naturally preferred. The dose level should vary from 1 to 50 mg./dose given from 1 to 4 times a day with a total daily dosage of 1 to 200 mg./day/human.

We claim:

1. A compound of the formula $$R-O-CH-CH_2-CH_2-N(CH_3)_2$$
$$|$$
$$phenyl$$

wherein R is p-chlorophenyl, p-tolyl or p-trifluoromethylphenyl, and pharmaceutically-acceptable acid addition salts thereof.

2. A compound according to claim 1, said compound being N,N-dimethyl-3-(p-trifluoromethylphenoxy)-3-phenylpropylamine.

3. A pharmaceutically-acceptable acid addition salt of a compound according to claim 2.

4. A compound according to claim 1, said compound being 3-(p-chlorophenoxy)-3-phenylpropyl dimethylamine.

5. 3-(o-tolyloxy)-3-phenylpropyldimethylamine and pharmaceutically-acceptable acid addition salts thereof.

* * * * *